United States Patent
Green, II (10) Patent No.: US 9,301,794 B2
(45) Date of Patent: Apr. 5, 2016

(54) MODULAR IMPACTOR HEAD

(71) Applicant: MICROPORT ORTHOPEDICS HOLDINGS INC., Tiel (NL)

(72) Inventor: John Michael Green, II, Arlington, TN (US)

(73) Assignee: MicroPort Orthopedic Holdings, Inc., Arlington, TN (US)

( * ) Notice: Subject to any disclaimer, the term of this patent is extended or adjusted under 35 U.S.C. 154(b) by 0 days.

(21) Appl. No.: 14/697,144

(22) Filed: Apr. 27, 2015

(65) Prior Publication Data

US 2015/0230849 A1    Aug. 20, 2015

Related U.S. Application Data

(63) Continuation of application No. 14/295,972, filed on Jun. 4, 2014, now Pat. No. 9,186,196, which is a continuation of application No. 13/111,450, filed on May 19, 2011, now Pat. No. 8,758,360.

(60) Provisional application No. 61/350,667, filed on Jun. 2, 2010.

(51) Int. Cl.
*A61B 17/92* (2006.01)
*A61B 17/00* (2006.01)

(52) U.S. Cl.
CPC .............. *A61B 17/921* (2013.01); *A61B 17/92* (2013.01); *A61B 2017/00473* (2013.01); *A61B 2017/922* (2013.01); *A61B 2017/924* (2013.01)

(58) Field of Classification Search
CPC ................. A61B 2017/00473; A61B 17/1666; A61B 17/92; A61B 17/921; A61B 2017/922; A61B 2017/924
See application file for complete search history.

(56) References Cited

U.S. PATENT DOCUMENTS

| | | | |
|---|---|---|---|
| 2,674,286 A | 4/1954 | Carson | |
| 3,618,678 A | 11/1971 | Smith | |
| 4,581,961 A | 4/1986 | Lai | |
| 5,100,407 A | 3/1992 | Conrad et al. | |
| 5,571,111 A | 11/1996 | Aboczky | |
| 5,630,819 A | 5/1997 | Ashby | |
| 5,918,821 A | 7/1999 | Grooms | |
| 5,934,384 A | 8/1999 | Wang | |
| 6,367,854 B1 | 4/2002 | Chou | |
| 6,890,336 B2 | 5/2005 | Nordman | |
| 7,037,310 B2 | 5/2006 | Murphy | |
| 7,115,119 B2 * | 10/2006 | Desarzens | A61B 17/1666 606/1 |
| 7,247,158 B2 | 7/2007 | Harris, Jr. | |
| 7,621,921 B2 | 11/2009 | Parker | |
| 8,220,135 B2 | 7/2012 | Vogel et al. | |
| 8,795,287 B2 | 8/2014 | Fritzinger et al. | |
| 2003/0229357 A1 | 12/2003 | Dye | |
| 2007/0163084 A1 | 7/2007 | Liou | |
| 2008/0097455 A1 | 4/2008 | Wright et al. | |
| 2008/0308600 A1 | 12/2008 | Kana | |
| 2009/0088757 A1 * | 4/2009 | Tulkis | A61B 17/1666 606/81 |
| 2009/0099566 A1 | 4/2009 | Maness et al. | |
| 2011/0083536 A1 | 4/2011 | Palmisano | |

* cited by examiner

*Primary Examiner* — Larry E Waggle, Jr.
(74) *Attorney, Agent, or Firm* — Adams and Reese LLP (57) ABSTRACT

A modular impactor head includes a load transfer member, a base, and a locking assembly. The base defines a space sized and configured to receive the load transfer member therein and to constrain movement of the load transfer member relative to the base in a plurality of directions. The locking assembly is sized and configured to constrain movement of the load transfer member with respect to the base in at least one direction such that the load transfer member is fixed to the base.

20 Claims, 12 Drawing Sheets

MODULAR IMPACTOR HEAD

CROSS-REFERENCE TO RELATED APPLICATIONS

This application is a continuation of U.S. patent application Ser. No. 14/295,972, filed on Jun. 4, 2014, which is a continuation of U.S. patent application Ser. No. 13/111,450, filed on May 19, 2011 claiming priority to U.S. provisional patent application 61/350,667, filed on Jun. 2, 2010, each of which is herein incorporated by reference in its entirety.

FIELD OF DISCLOSURE

The disclosed system and method relate to impactors for implants. More specifically, the disclosed system and method relate to a modular impactor head for an implant impactor.

BACKGROUND

Medical implants that are to be received within an intramedullary canal are frequently installed with the aid of tools for creating the intramedullary canal and inserting the implant within the canal. Such insertion tools include implant impaction instruments referred to as "impactors".

Conventional impactors have a load transfer member fixed to a handle. Typically, the load transfer device is fixed to the handle by cross-pinning the load transfer device to an impactor head. However, the load transfer members have a high incidence of wear, which has prompted the development of modular assemblies. These modular assemblies typically employ a set screw assembly to maintain the load transfer member coupled to the impactor head. While these modular assemblies enable the load transfer members to be replaced when worn, the set screw assemblies are highly susceptible to fatigue, which may result in failure.

Additionally, conventional impactor handles are frequently fabricated from metals due to the high structural integrity and the ability to machine and weld metals to form the desired device. However, forming impactor handles from metals results in the impactor having considerable weight and may be difficult for less strong surgeons to manipulate.

Accordingly, an improved impactor design is desirable.

SUMMARY

A modular impactor head is provided including a load transfer member, a base, and a locking assembly. The base defines a space sized and configured to receive the load transfer member therein and to constrain movement of the load transfer member relative to the base in a plurality of directions. The locking assembly is sized and configured to constrain the movement of the load transfer member with respect to the base in at least one direction such that the load transfer member is fixed to the base.

Also disclosed is a modular impactor head including a load transfer member and a base including a plurality of sidewalls. The sidewalls extend from a bottom wall of the base to define a space sized and configured to receive the load transfer member. At least two of the sidewalls define slots and the bottom wall defines a cavity. The slots of the sidewalls are sized and configured to cooperate with tabs extending from the load transfer member. A locking assembly is sized and configured to be received within the cavity and to lock the load transfer member to the base.

A method is also disclosed in which a biasing member is inserted into a cavity defined by a bottom wall of a body of a modular impactor head. The modular impactor head includes a plurality of sidewalls extending from the bottom wall. A space is defined by the plurality of sidewalls and the bottom wall. A locking shaft is inserted into the cavity, and a tab extending from a surface of a load transfer member is aligned with a slot defined by one of the sidewalls. The load transfer member is inserted into the space in a first direction such that the tab is received within the slot. The load transfer member is slid in a second direction until the locking shaft is received within a hole defined by the load transfer member.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein.

DETAILED DESCRIPTION

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Figure 1:
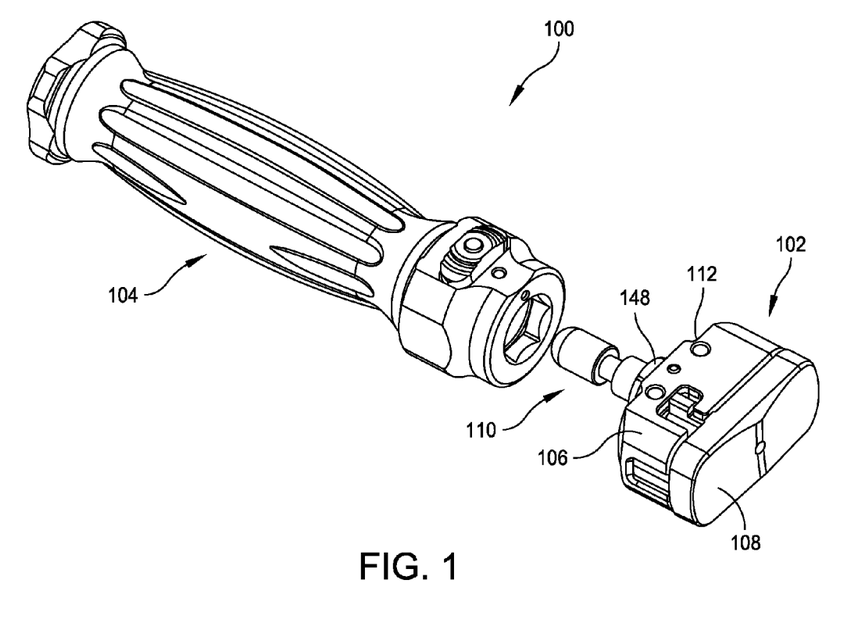
FIG. 1 is a partially exploded isometric view of one example of a modular implant impactor.

FIG. 1 illustrates one example of an improved impactor 100. As shown in FIG. 1, impactor 100 includes an impactor head assembly 102 that may be releaseably coupled to a handle assembly 104. Impactor head assembly 102 includes a base 106 that may be releasably coupled to a load transfer member 108. A coupling member 110 extends from a proximal portion 112 of base 106 of impactor head 102 for coupling to handle 104.

Figure 2:
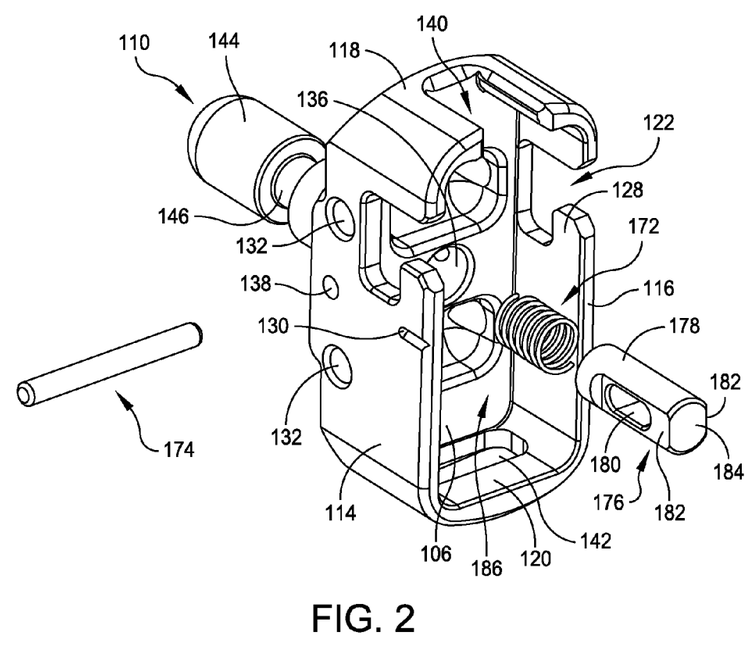
FIG. 2 is an exploded isometric view of a base and a locking assembly of a modular impactor head in accordance with the modular implant impactor illustrated in FIG. 1.
Figure 3:
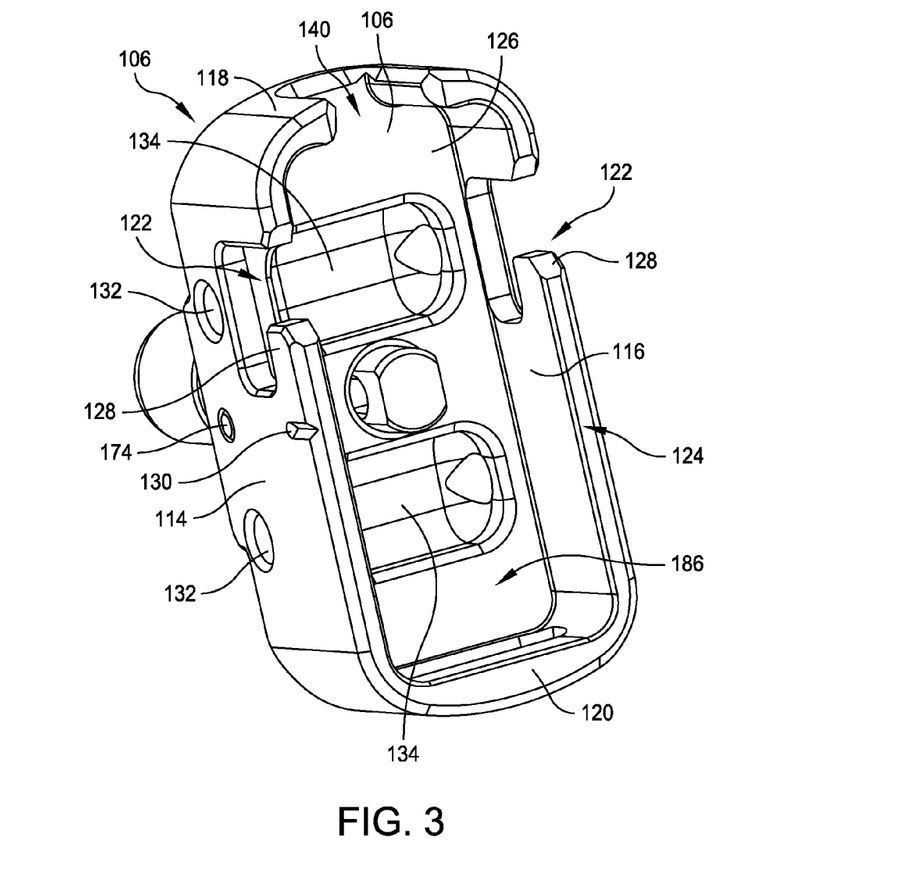
FIG. 3 is an end view of the base and the locking assembly of the modular impactor head illustrated in FIG. 2 when assembled.
Figure 4:
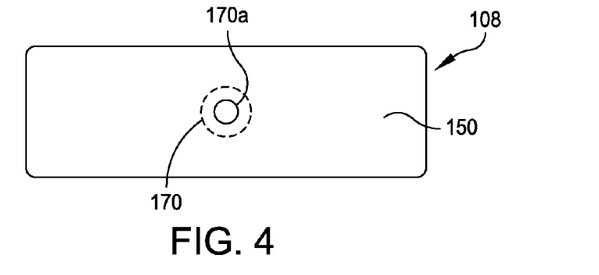
FIG. 4 is a top side view of a load transfer member in accordance with the modular implant impactor illustrated in FIG. 1.

As best seen in FIGS. 2 and 3, a plurality of sidewalls 114, 116, 118, and 120 extend in a distal direction from base 106, which has a substantially rectangular shape. Lengthwise sidewalls 114 and 116 each define a slot 122 extending from a distal edge 124 to a bottom wall 126 where a width of the slot increases to form tabs 128 as shown in FIG. 3. One or both of lengthwise sidewalls 114, 116 may include an alignment feature 130 in the form of a notch, scribe line, dimple, or other discernable indicia located at an approximate mid-point of the length. Sidewall 114 defines one or more holes 132 that extend through sidewall 114 and communicate with depressions 134 disposed on either side of cavity 136 in bottom wall 126 as best seen in FIG. 2. Sidewalls 114 and 116 also define a through hole 138.

Sidewall 118 includes a slot 140 disposed approximately at the midpoint between sidewall 114 and sidewall 116. In some embodiments, slot 140 extends from distal edge 124 to bottom wall 126. Still referring to FIG. 2, sidewall 120 defines an aperture 142 having a rectangular shape, although one skilled in the art will understand that aperture 142 may have other shapes including, but not limited to, oval, round, triangular, pentagonal, and hexagonal, to name a few.

As best seen in FIGS. 1 and 2, coupling member 110 extends from rectangular base 106 in a proximal direction, i.e., in an opposite direction with respect to the direction in which sidewalls 114-120 extend. Coupling member 110 may have a body 144 with a circular cross-sectional geometry and include a reduced diameter area 146 disposed along its length and a rounded taper at one end. As best seen in FIGS. 1 and 9-11, shoulder 148 may have a cross-sectional geometry that prevents rotation. For example, shoulder 148 may have a rectangular, pentagonal, hexagonal, or other cross-sectional geometry. In some embodiments, shoulder 148 has a round cross-sectional geometry including one or more flats for preventing rotation of impactor head 102 with respect to impactor handle 104 as described below.

Figure 5:
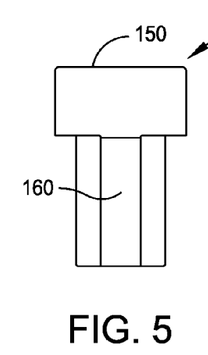
FIG. 5 is an end view of the load transfer member illustrated in FIG. 4.
Figure 6:
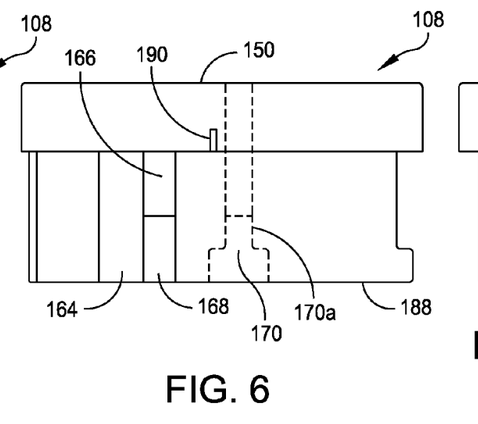
FIG. 6 is a side view of the load transfer member illustrated in FIG. 4.
Figure 7:
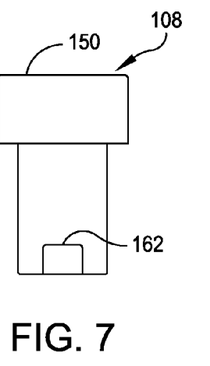
FIG. 7 is an end view of the load transfer member illustrated in FIG. 4.
Figure 8:
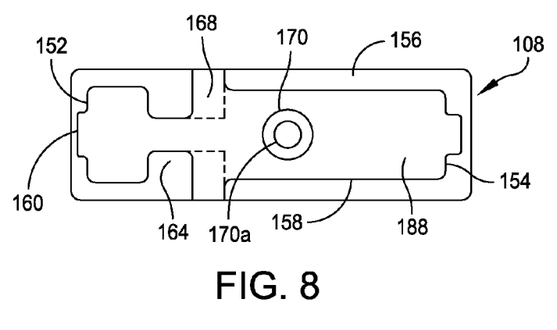
FIG. 8 is a bottom side view of the load transfer member illustrated in FIG. 4.

FIGS. 4-8 illustrate various views of load transfer member 108, which is preferably fabricated from a polymer material in order to prevent damage to an implant. As shown in FIGS. 4-8, load transfer member 108 has a substantially rectangular impact surface 150 with sidewalls 152, 154, 156, and 158 extending therefrom. Sidewall 152 includes a protrusion 160 extending from rectangular impact surface and being sized and configured to be received within slot 140 defined by sidewall 118 of base 106 as best seen in FIGS. 5 and 8. FIGS. 7 and 8 illustrate rectangular detent 162 extending from sidewall 154 that is sized and configured to be received in aperture 142 defined by sidewall 120 of base 106. Sidewalls 156 and 158 may have an identical structure including channel 164 and a cutout 166, which defines a tab 168 as best seen in FIGS. 1 and 6. In some embodiments, sidewall 154 may be cylindrical or have another geometry and be configured to constrain load transfer member 108 in multiple degrees of freedom as will be understood by one skilled in the art. Bottom surface of load transfer member 108 defines a hole 170. In some embodiments, hole 170 is a blind hole. In other embodiments, hole 170 extends through load transfer member 108 and includes a reduced diameter section 170a in order to permit access to a locking mechanism for disassembling impactor head 102 as described below.

Referring again to FIG. 2, impactor head assembly 102 includes a spring or biasing member 172, a pin 174, and a locking shaft 176. Biasing member 172 is selected to have a diameter sized and configured to be received within cavity 136 in base 106. Pin 174 has a diameter such that it may be press fit within through hole 138 defined by sidewalls 114 and 116. Locking shaft 176 has an elongate body 178 with a circular cross-sectional geometry that is sized and configured to be received within cavity 136. Elongate body 178 defines a slot 180 having a width that is sufficiently sized to receive pin 174 therein. One or more flats 182 may be formed on opposing sides of elongate body 178 such that slot 180 extends through flats 182 as best seen in FIG. 2.

Figure 9:
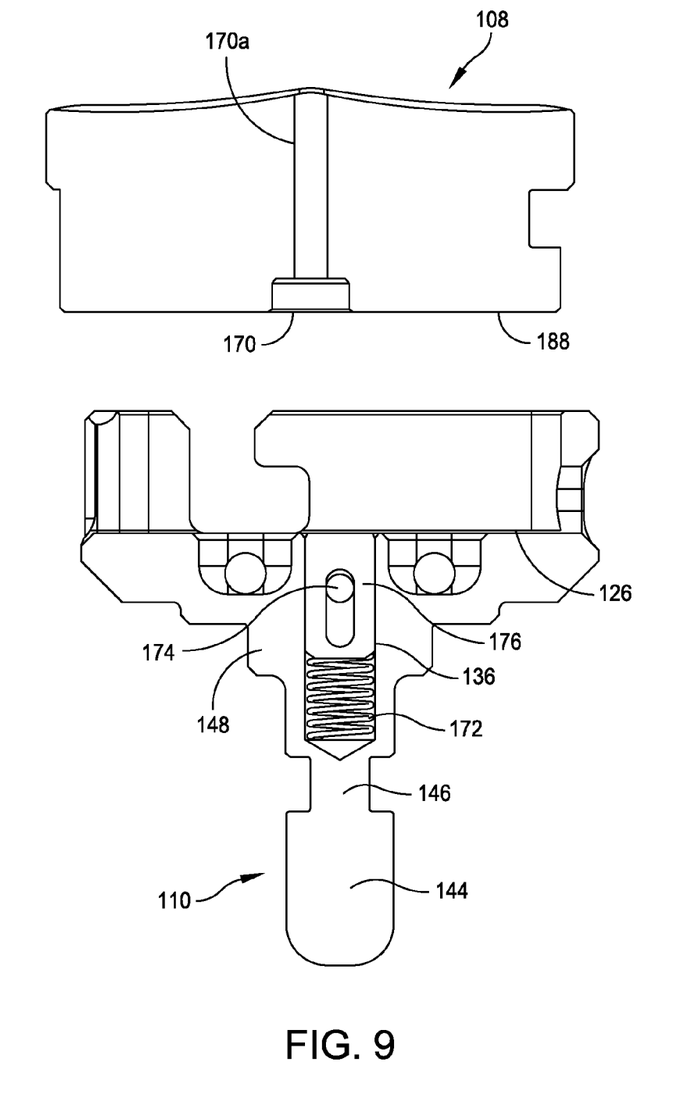
FIG. 9 is a partially exploded cross-sectional view of the modular impactor head illustrated in FIG. 2.

To assemble impactor head assembly 102, biasing member 172 is inserted into cavity 136 defined by base 106 as illustrated in FIGS. 2 and 9. Locking shaft 176 is then inserted into cavity 136 compressing biasing member 172 (FIGS. 3 and 9). The one or more flats 182 may be used to align slot 180 of locking shaft 176 with through hole 138 in base 106. With locking shaft 176 disposed within cavity 136, pin 174 is inserted into cavity 136. Locking shaft 176 may be depressed such that end 184 is approximately even with bottom wall 126 of base 106 in order to enable pin 174 to be received within slot 180 of locking shaft 176.

Figure 10:
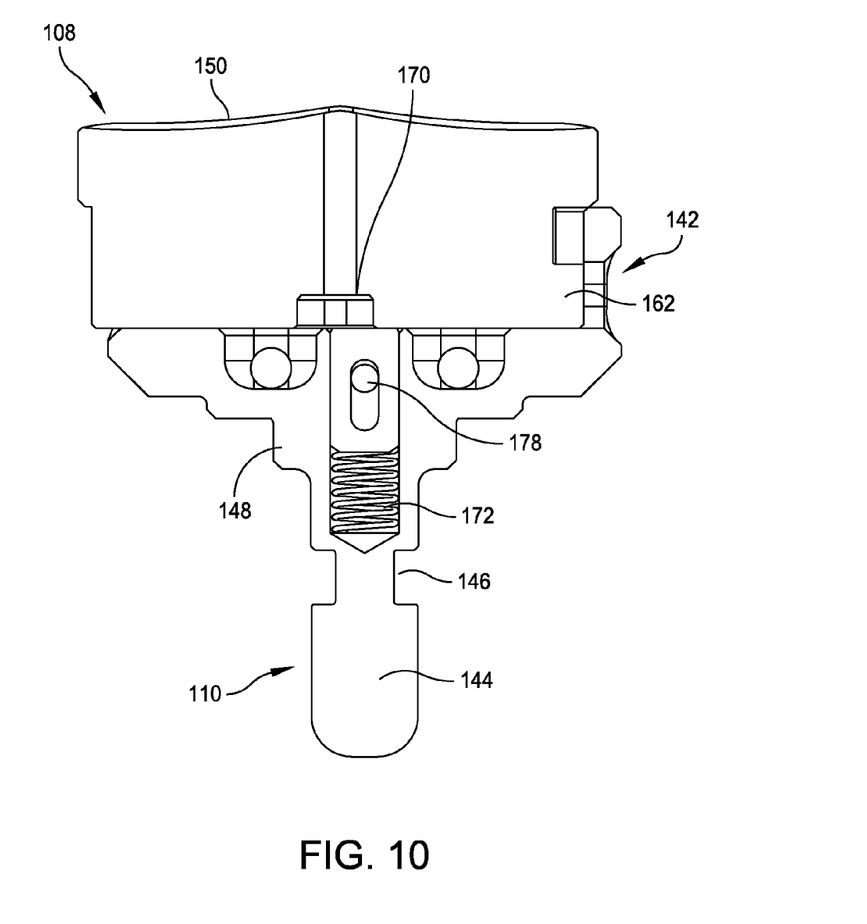
FIG. 10 is a cross-sectional view of the modular impactor head illustrated in FIG. 2 during assembly.

Load transfer member 108 is then loaded into the space 186 defined by sidewalls 114-120 of base 106 by aligning rectangular protrusion 160 of load transfer member 108 with slot 140 defined by sidewall 118 of base 106 and aligning tabs 168 of load transfer member 108 with slots 122 defined by sidewalls 114 and 116 of base 106. As load transfer member 108 is slid into engagement with base 106 as shown in FIGS. 9 and 10, the bottom wall 188 may contact end 184 of locking shaft 176 causing locking shaft 176 to be completely disposed within cavity 136.

Load transfer member 108, which may also include an alignment feature 190 in the form of a notch, scribe line, dimple, or other discernable indicia located approximately at a mid-point of the length, is slid relative to base 106 until alignment feature 190 is aligned with alignment feature 130 at which point detent 162 of load transfer member 108 is received within aperture 142 defined by sidewall 120 and tabs 128 of base 106 engage tabs 168 of load transfer member 108.

Figure 11:
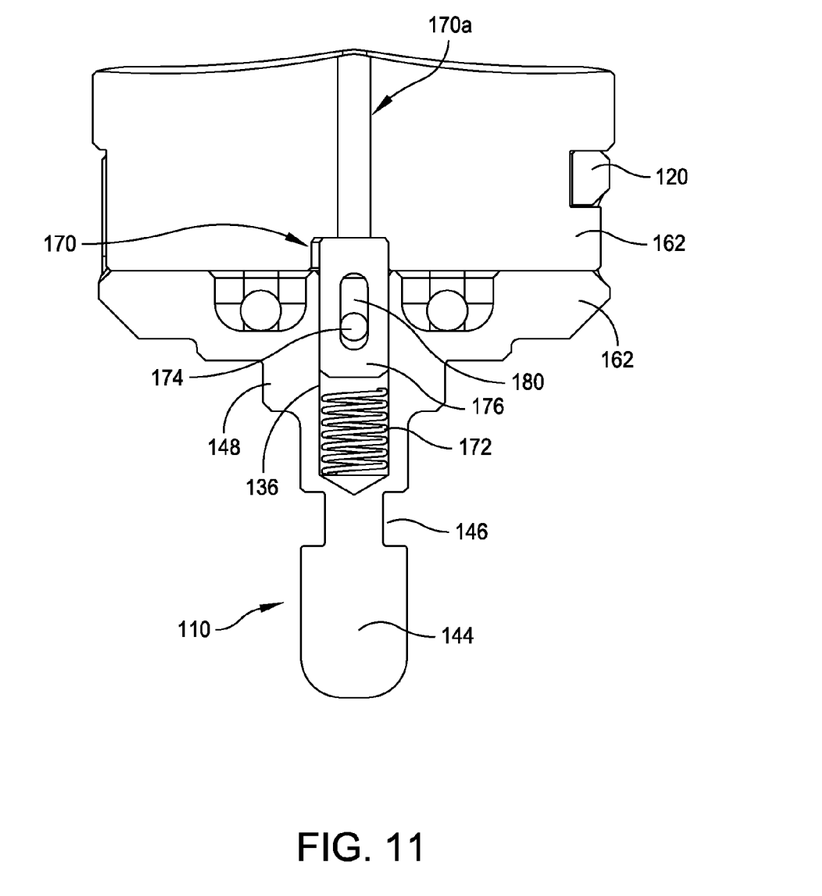
FIG. 11 is a cross-sectional view of the modular impactor head illustrated in FIG. 2 after assembly.

When the alignment features 130 and 190 are aligned, base 106 limits all but one degree of movement of load transfer member 108 as sidewalls 114, 116, and 120 and bottom wall 126 prevent rotation, movement towards base 106, and lateral movement in all directions except for one, i.e., movement towards sidewall 118. Additionally, tabs 128 and aperture 142 of base 106 prevent movement of load transfer member 108 away from base 106. Thus, the only direction in which load transfer member 108 may move with respect to base 106 when alignment features 130 and 190 are aligned is towards sidewall 118. However, the locking mechanism provided by biasing member 172, pin 174, and locking shaft 178 constrains the movement of load transfer member 108 from being slid in the direction of sidewall 118 such that load transfer member 108 is fixed to base 106. The locking mechanism engages load transfer member 108 by biasing member 172 forcing locking shaft 178 into hole 170 defined by the bottom surface 188 of load transfer member 108 as best seen in FIG. 11.

Impactor head 102 may be sterilized using an autoclave or other device either before or after being assembled as will be understood by one skilled in the art. Slots 122 of base 106, channel 164 of load transfer member 108, and holes 132 and depressions 134 defined by base 106 communicate with each other to provide a conduit for fluid to exit the modular impactor head 102.

Figure 12:
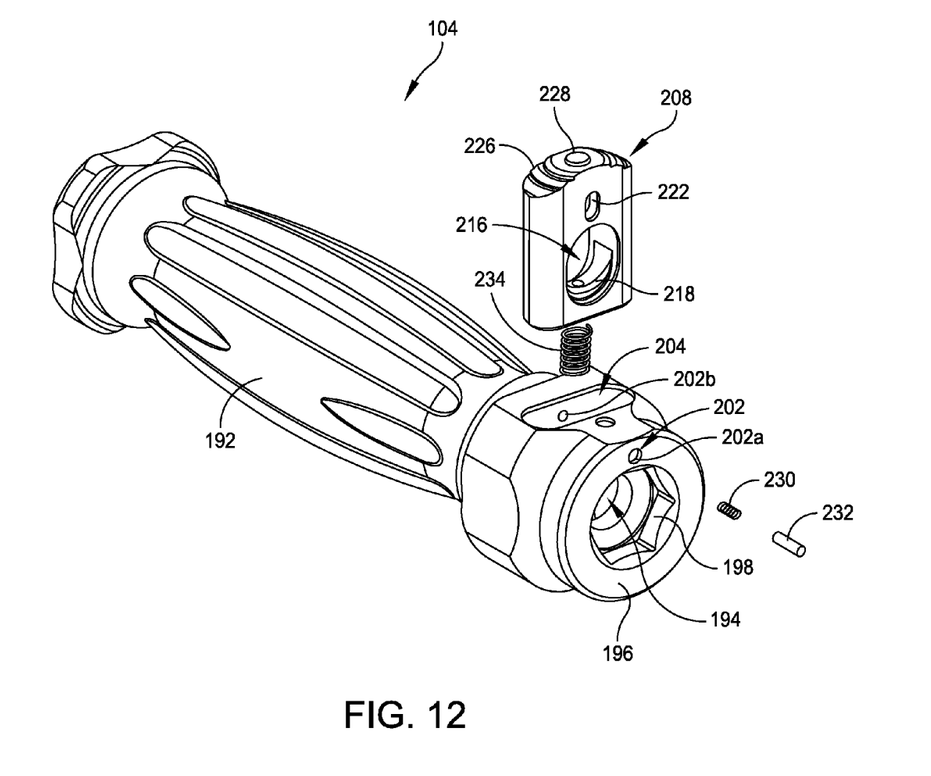
FIG. 12 is an exploded isometric view of a modular impactor handle in accordance with FIG. 1.
Figure 13:
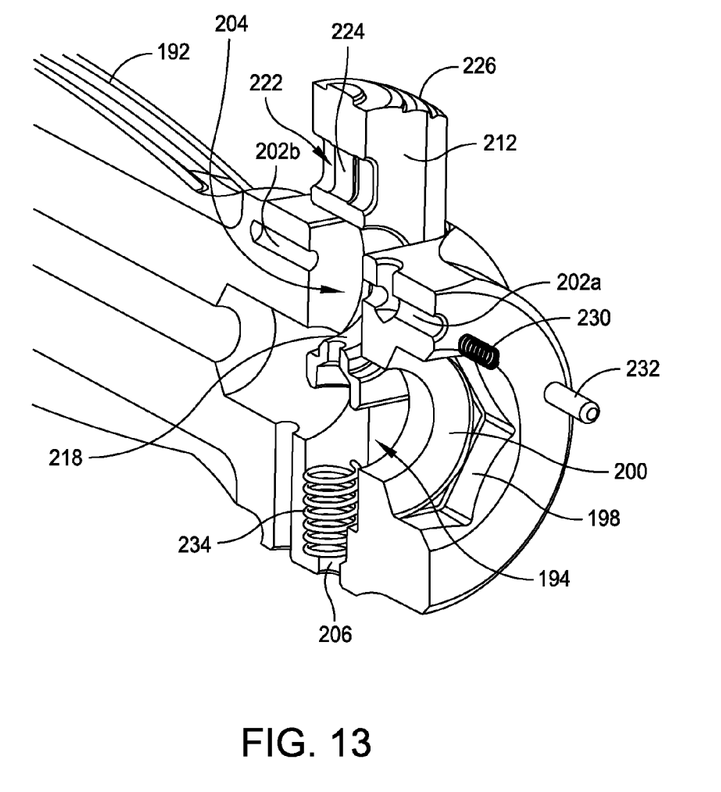
FIG. 13 is a cross-sectional view of the modular impactor handle illustrated in FIG. 12 during assembly.
Figure 14:
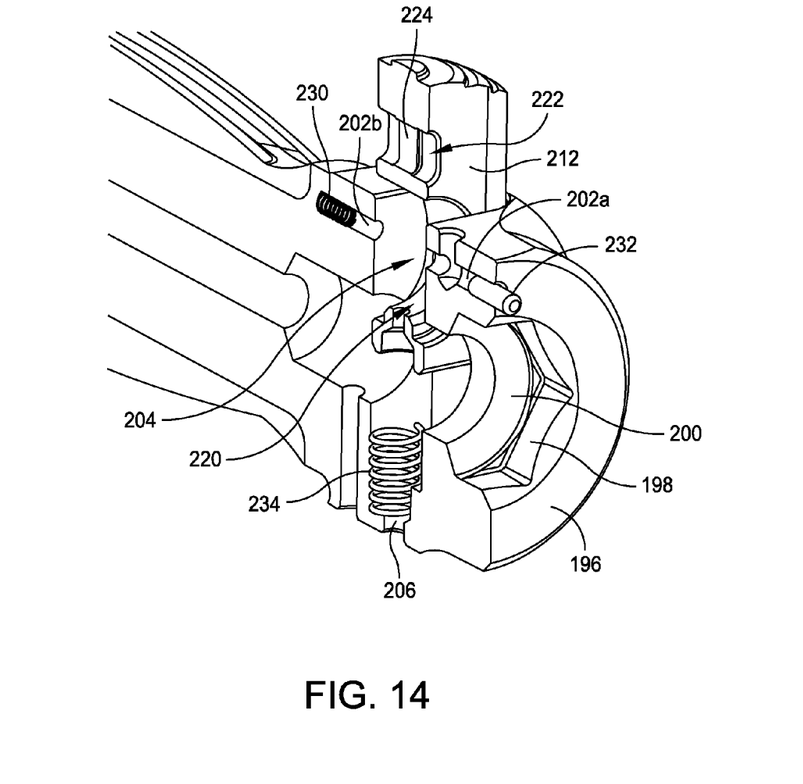
FIG. 14 is a cross-section view of the modular impactor handle illustrated in FIG. 12 at another stage of assembly.

FIG. 12 illustrates handle assembly 104, which includes a handle body 192 defining an opening 194 at one end 196. Opening 194 has an internal diameter that is sufficiently large so as to receive coupling member 110 of impactor head assembly 102. In some embodiments, opening 194 may extend through handle body 192 to facilitate drying of handle 192 after sterilization. Opening 194 also includes an anti-rotation feature 198, which complements the geometry of shoulder 148 of coupling member 110. For example, anti-rotation feature 198 may be an internal hexagonal geometry as shown in FIGS. 12-14, a single flat disposed on the interior of opening 196, or any other geometry or feature for preventing rotation of impactor head assembly 102 with respect to handle assembly 104. Opening 194 may also include an internal shoulder 200 disposed adjacent to anti-rotation feature as best seen in FIG. 13.

End 196 of body 192 defines a hole 202 adjacent to opening 194 as illustrated in FIG. 12. Hole 202 communicates with slot 204 formed along the length of body 192 and includes a first portion 202a disposed on one side of slot 204 and a second portion 202b disposed on the other side of slot 204. Slot 204 has an oblong or rectangular shape that is sized and configured to receive locking button 208 and to intersect opening 194 and hole 202. As best seen in FIGS. 13 and 14, a cavity 206 is disposed at the bottom 210 of slot 204.

Locking button 208 has a rectangular shape with a cross-sectional geometry that is complementary to the geometry of slot 204 with substantially flat front and back surfaces 212 and 214. An aperture 216 is formed through locking button 208 and includes a locking bar 218 along its inner surface 220 as best seen in FIGS. 13 and 14, which may be in the form of a reduced diameter area or a raised surface extending along an interior of aperture 216. A groove 222 may be formed through, or in the back surface 214 of, locking button 208. If groove 222 is formed through locking button 208, then it may include an area 224 having a reduced size as best seen in FIGS. 13 and 14. Upper surface 226 of locking button 208 may be textured or include a frictional feature 228 to facilitate manipulation by a user.

Figure 15:
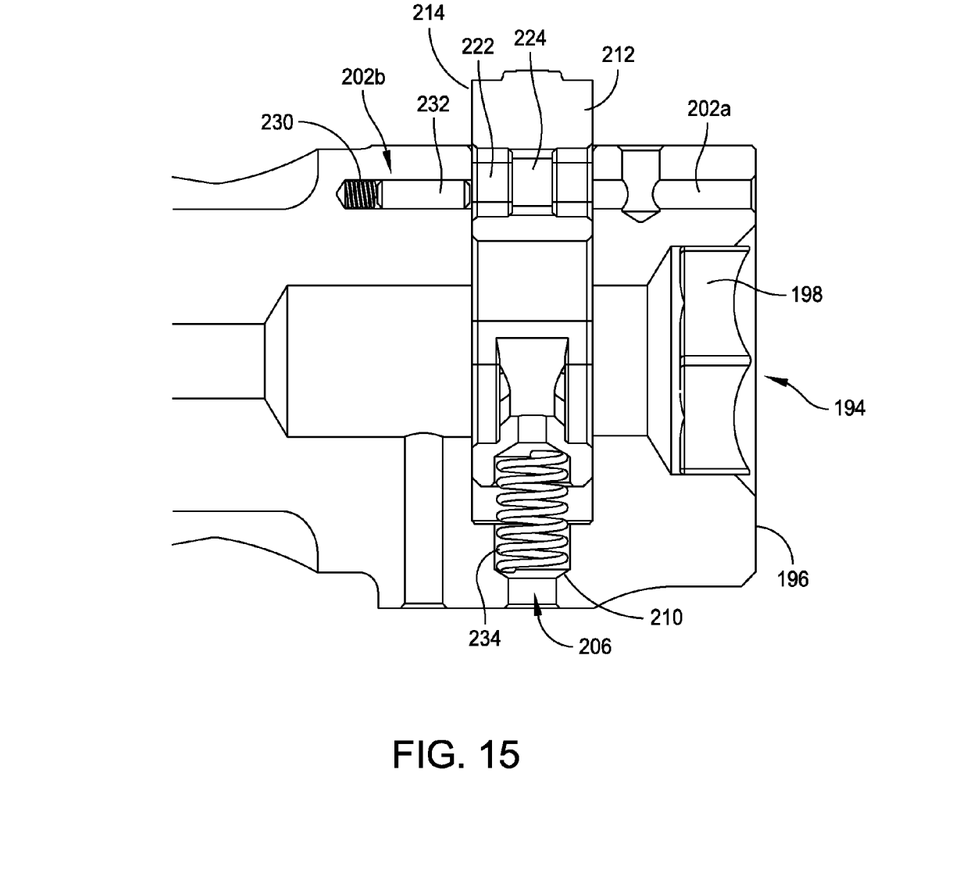
FIG. 15 is a cross-sectional view of the modular impactor handle illustrated in FIG. 12 at another stage of assembly.

To assemble handle 104, a retaining pin biasing member 230, which may be a coil spring or other device for biasing or otherwise applying a force on a retaining pin 232, is inserted into hole 202. A locking bar biasing member 234 is inserted into slot 204 until it is received in cavity 206 as best seen in FIG. 13. Locking button 208 is inserted into slot 204 until aperture 216 aligns with hole 202 at which point retaining pin 232 is inserted into hole 202a and received in hole 202b as illustrated in FIGS. 14 and 15. The locking bar retaining mechanism comprising retaining pin biasing member 230 and retaining pin 232 are compressed into hole 202b by inserting a thin elongate rod into hole 202 to force retaining pin 232 into pin biasing member 230 until retaining pin 232 is disposed within hole 202b to enable locking button 208 to be further received in slot 204 as shown in FIG. 15.

Figure 16:
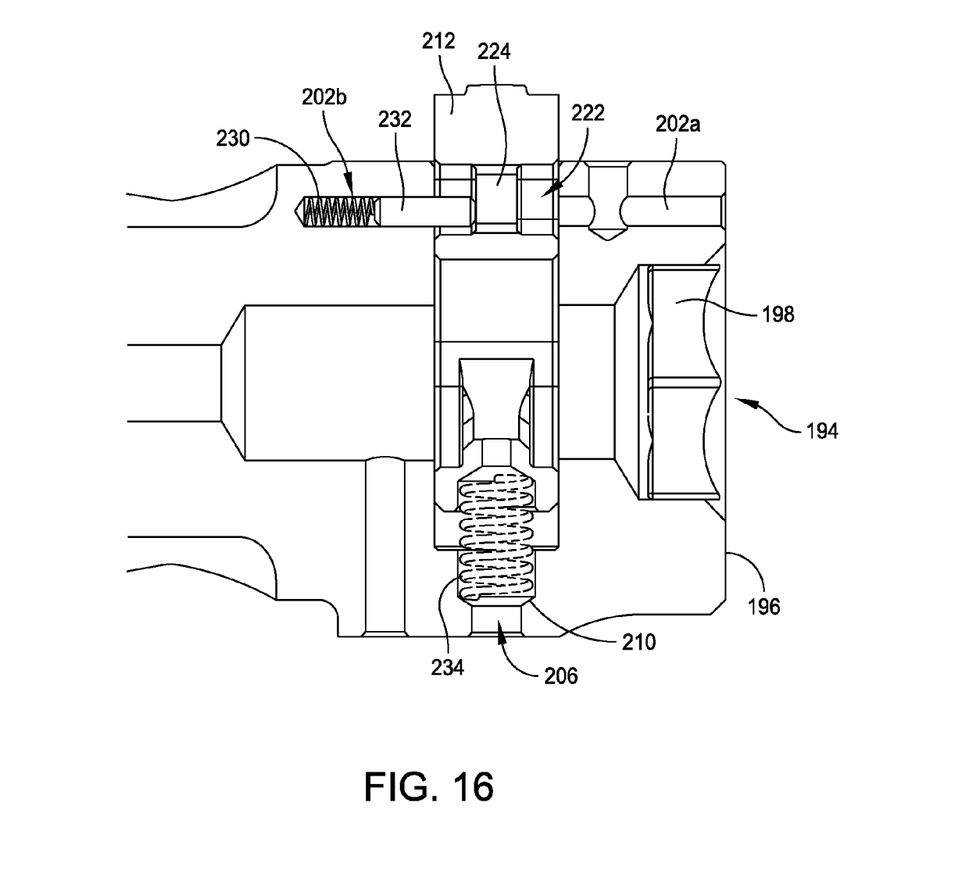
FIG. 16 is a cross-sectional view of the assembled modular impactor handle.

As locking button 208 is further received in slot 204, groove 222, defined by locking button 208, aligns with hole 202b resulting in retaining pin 232 being received within groove 222 as retaining pin biasing member 230 applies a force on retaining pin 232 toward groove 222. Area 224 engages retaining pin 232 to maintain retaining pin 232 and retaining pin biasing member 230 within hole 202b as best seen in FIG. 16. With retaining pin 232 received within groove 222, locking button 208 is retained within slot 204, but may slide within slot 204 a distance defined by a length of groove 222.

Impactor 100 is assembled by coupling impactor head assembly 102 to handle 104 by inserting coupling member 110 of impactor head 102 into opening 194 of handle 104. As coupling member 110 slides into opening 194, body 144 of coupling member 110 contacts locking bar 218 of locking button 208, which results in locking button 208 being received more deeply within slot 204 until aperture 216 of locking button 208 aligns with opening 194. Locking bar biasing member 234 compresses from the force applied by locking button 208. When reduced diameter area 146 of coupling member 110 aligns with locking bar 218, which occurs when anti-rotation feature 198 of opening 194 aligns with corresponding geometry of shoulder 148, locking bar biasing member 234 forces locking bar 208 into engagement with reduced diameter area 146.

The engagement between reduced diameter area 146 and locking bar 208 prevents axial movement of impactor head assembly 102 along an axis defined by opening 194 with respect to handle 104 to maintain impactor head assembly 102 coupled to handle 104. The engagement between shoulder 148 of impactor head assembly 102 and anti-rotation feature 198 of handle 104 prevents rotational movement by impactor head 102 with respect to handle 104.

Once assembled, impactor 100 may be used as any implant impactor as would be understood by one skilled in the art. Impactor head 102 may be disconnected from handle 104 by applying a downward force on locking button 208, which forces locking button 208 deeper into slot 204, until aperture 216 aligns with opening 194 and then axially pulling impactor head 102 away from handle 104.

Load transfer member 108 may advantageously be replaced if it becomes worn. To remove load transfer member 108 from base 106, a thin rod (not shown) may be used through hole 170 to remove pin 174 from its engagement with slot 180 of locking shaft 176. With pin 174 disengaged from locking shaft 176, the thin rod may be inserted into hole 170 in load transfer member 108 to contact the end 184 of elongate body 178 and compress biasing member 172 until end 184 is disposed within cavity 136. With locking shaft 176 disposed within cavity 136, load transfer member 108 may be slid in the direction of sidewall 118 until detent 162 is disengaged from aperture 142 defined by sidewall 120 and tabs 168 of load transfer member 108 are disengaged from tabs 128 of body 106. Load transfer member 108 may then be removed from body 106 and replaced with another load transfer member 108 in accordance with the assembly process described above.

The modular impactor 100 described above may advantageously be fully disassembled and assembled while providing a more rugged and robust structure compared to conventional impactors that rely on set screw assemblies.

Additionally, handle assembly 104, and more particularly handle body 192, may be advantageously machined or molded from carbon reinforced plastic, which enables the weight of impactor 100 to be significantly reduced while retaining sufficient structural integrity, as the impactor handle assembly 104 does not require welding to join different parts together. However, one skilled in the art will understand that handle body 192 may be fabricated from other materials such as, for example, metals and polymers.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method, comprising:
   inserting a biasing member into a cavity defined by a bottom wall of a body of a modular impactor head, the modular impactor head including a plurality of sidewalls extending from the bottom wall that together define a space;
   inserting a locking shaft into the cavity;
   aligning a tab extending from a surface of a load transfer member with a slot defined by one of the sidewalls;
   inserting the load transfer member into the space in a first direction such that the tab is received within the slot; and
   sliding the load transfer member in a second direction until the locking shaft is received within a hole defined by the load transfer member.

2. The method of claim 1, further comprising inserting a pin into a hole defined by the body such that the pin is received within a slot defined by the locking shaft.

3. The method of claim 2, further comprising:
   applying a force to the pin to disengage the pin from the slot defined by the locking shaft;
   sliding the load transfer member in a third direction until the tab of the load transfer member is aligned with the slot defined by the sidewall; and
   removing the load transfer member from the space defined by the sidewalls.

4. The method of claim 3, further comprising applying a force to an end of the locking shaft to compress the biasing member and to disengage the locking shaft from the hole defined by the load transfer member.

5. The method of claim 1, wherein a coupling member extends from the body of the modular impactor head in an opposite direction with respect to the first direction.

6. The method of claim 5, further comprising inserting the coupling member into an opening of a handle.

7. The method of claim 6, wherein the coupling member comprises a reduced diameter area, and wherein a locking member is sized and configured to interface with the reduced diameter area of the coupling member when the coupling member is inserted into the opening.

8. The method of claim 7, further comprising applying a force to a locking button to release the coupling member from the locking member.

9. The method of claim 6, wherein the opening defines an anti-rotation feature to prevent rotation of the modular impactor head with respect to the handle.

10. The method of claim 9, wherein the anti-rotation feature comprises a geometry complementary with respect to a shoulder of the coupling member.

11. A method, comprising:
    inserting a biasing member into a cavity defined by a bottom wall of a body of a modular impactor head, the modular impactor head including a plurality of sidewalls extending from the bottom wall that together define a space sized and configured to receive a load transfer member therein and to constrain movement of the load transfer member relative to the body;
    inserting a locking shaft into the cavity;
    aligning a first tab extending from a surface of the load transfer member with a first slot defined by a first of the plurality of sidewalls;
    aligning a second tab extending from the surface of the load transfer member with a second slot defined by a second of the plurality of sidewalls; and
    inserting the load transfer member into the space in a first direction such that the first tab is received within the first slot and the second tab is received within the second slot; and
    sliding the load transfer member in a second direction until the locking shaft is received within a hole defined by the load transfer member.

12. The method of claim 11, further comprising inserting a pin into a hole defined by the body such that the pin is received within a slot defined by the locking shaft.

13. The method of claim 12, further comprising:
    applying a force to the pin to disengage the pin from the slot defined by the locking shaft;
    sliding the load transfer member in a third direction until the first and second tabs of the load transfer member are aligned with the first and second slots defined by the first and second of the plurality of sidewalls; and
    removing the load transfer member from the space defined by the sidewalls.

14. The method of claim 13, further comprising applying a force to an end of the locking shaft to compress the biasing member and to disengage the locking shaft from the hole defined by the load transfer member.

15. The method of claim 11, wherein a coupling member extends from the body of the modular impactor head in an opposite direction with respect to the first direction.

16. The method of claim 15, further comprising inserting the coupling member into an opening of a handle.

17. The method of claim 16, wherein the coupling member comprises a reduced diameter area, and wherein a locking member is sized and configured to interface with the reduced diameter area of the coupling member when the coupling member is inserted into the opening.

18. The method of claim 17, further comprising applying a force to a locking button to release the coupling member from the locking member.

19. The method of claim 16, wherein the opening defines an anti-rotation feature to prevent rotation of the modular impactor head with respect to the handle.

20. A method, comprising:
    inserting a biasing member into a cavity defined by a bottom wall of a body of a modular impactor head, the modular impactor head including a plurality of sidewalls extending from the bottom wall that together define a space, wherein a coupling member extends from the bottom wall of the body in a first direction;
    inserting a locking shaft into the cavity;
    aligning a tab extending from a surface of a load transfer member with a slot defined by one of the sidewalls;
    inserting the load transfer member into the space in a second direction such that the tab is received within the slot, wherein the second direction is an opposite direction with respect to the first direction;

sliding the load transfer member in a third direction until the locking shaft is received within a hole defined by the load transfer member;

inserting the coupling member into an opening of a handle, wherein a locking member is sized and configured to interface with a reduced diameter area of the coupling member when the coupling member is inserted into the opening.

\* \* \* \* \*